(12) United States Patent
Yamao et al.

(10) Patent No.: US 7,326,579 B2
(45) Date of Patent: *Feb. 5, 2008

(54) IMMUNOASSAY METHOD FOR LYZED WHOLE BLOOD

(75) Inventors: Yasuo Yamao, Miyanohigashi-machi (JP); Narihiro Oku, Miyanohigashi-machi (JP)

(73) Assignee: Horiba, Ltd., Kyoto (JP)

( * ) Notice: Subject to any disclaimer, the term of this patent is extended or adjusted under 35 U.S.C. 154(b) by 452 days.

This patent is subject to a terminal disclaimer.

(21) Appl. No.: 11/026,830

(22) Filed: Dec. 30, 2004

(65) Prior Publication Data

US 2005/0118732 A1 Jun. 2, 2005

Related U.S. Application Data

(62) Division of application No. 09/511,824, filed on Feb. 24, 2000, now Pat. No. 6,855,562, which is a division of application No. 08/914,039, filed on Jul. 28, 1997, now Pat. No. 6,030,845.

(30) Foreign Application Priority Data

Jul. 30, 1996 (JP) .................................. 8-217966

(51) Int. Cl.
*G01N 33/543* (2006.01)
(52) U.S. Cl. ...................... 436/523; 436/518; 436/523; 436/524; 436/528; 435/7.1; 435/7.25; 435/287.2; 422/44; 422/55; 422/69; 422/73; 356/39; 356/40; 356/41; 356/42
(58) Field of Classification Search ................. 435/7.1, 435/7.25, 287.1, 287.2; 436/518, 523, 524, 436/528, 529, 17, 18, 164, 177; 422/55, 422/57, 73, 82.05
See application file for complete search history.

(56) References Cited

U.S. PATENT DOCUMENTS

| 3,569,721 A | 3/1971 | Goldberg |
| 3,689,632 A | 9/1972 | Mizushima |
| 4,013,417 A | 3/1977 | Raffaele |
| 4,357,105 A | 11/1982 | Loretz |

(Continued)

FOREIGN PATENT DOCUMENTS

EP 0367475 5/1990

(Continued)

OTHER PUBLICATIONS

Abstract, "Production of Food Colourant for Marking Meant Portions . . . ", by T. P. Perkel, et al., Derwent Publishing, Feb. 9, 1995.

(Continued)

*Primary Examiner*—Gailene R. Gabel (57) ABSTRACT

The present invention provides an immunoassay method in which blood can be measured even without pretreatment by means of a centrifuge etc. In the present invention, antibodies or antigens in a sample are subjected to agglutination reaction with insoluble carriers onto which antigens or antibodies specifically reacting with the antibodies or antigens in the sample have been immobilized and the resulting agglutination mixture is determined for the change in its absorbance or in its scattered light by irradiation with light, wherein said sample is whole blood and the whole blood is forcibly lyzed.

3 Claims, 7 Drawing Sheets

U.S. PATENT DOCUMENTS

| | | | |
|---|---|---|---|
| 4,379,847 A | 4/1983 | Fruitstone et al. | |
| 4,889,815 A | 12/1989 | Bradwell et al. | |
| 4,997,769 A | 3/1991 | Lundsgaard | |
| 5,043,289 A | 8/1991 | Serres | |
| 5,541,117 A | 7/1996 | Karl et al. | |
| 5,729,333 A | 3/1998 | Osten et al. | |
| 5,731,206 A | 3/1998 | Ledis et al. | |
| 6,030,845 A * | 2/2000 | Yamao et al. | 436/533 |
| 6,855,562 B1 * | 2/2005 | Yamao et al. | 436/523 |

FOREIGN PATENT DOCUMENTS

| | | |
|---|---|---|
| JP | 57150382 | 9/1982 |
| JP | 60047962 A | 3/1985 |
| JP | 60-244861 A | 4/1985 |
| JP | 02-226067 | 9/1990 |
| JP | 07-035752 | 7/1995 |
| JP | 08-160048 | 6/1996 |
| JP | 09-274041 | 10/1997 |
| WO | 85-05640 | 12/1985 |

OTHER PUBLICATIONS

Schoessler et al., Development and Application of Latex-Agglutination Assay for the Determination of C-Reactive Protein, Zeitschrift fuer Klinische Medizin (Berlin), (1990), 45 (17) 1501-1504, Abstract Translated.

* cited by examiner

IMMUNOASSAY METHOD FOR LYZED WHOLE BLOOD

This application is a divisional of U.S. patent application Ser. No. 09/511,824 filed on Feb. 24, 2000 (now U.S. Pat. No. 6,855,562), which is a divisional application of U.S. Ser. No. 08/914,039 filed on Jul. 28, 1997 now U.S. Pat. No. 6,030,845 issued on Feb. 29, 2000.

BACKGROUND OF THE INVENTION

1. Field of the Invention

The present invention relates to an immunoassay method and in particular to an immunoassay method for use with lysed whole blood in which antibodies or antigens in a sample are subjected to agglutination reaction with insoluble carriers onto which antigens or antibodies specifically reacting with the antibodies or antigens in the sample have been immobilized. The resulting agglutination mixture is irradiated with near infrared or infrared rays to determine its change in absorbance or its change in scattered light.

2. Description of Related Art

Japanese Patent Publication No. 11575/1983 discloses a prior art method which comprises antigen-antibody reaction between antigen- or antibody-immobilized insoluble carriers and antibodies or antigens in a humor sample, then irradiating the reaction mixture with light with a wavelength of 600 to 2400 nm and measuring the increase in its absorbance. By virtue of its usefulness, this method has become the mainstream of immunoassay method at present as a so-called latex immunoturbidimetry.

However, the measurement sample used in said measurement method is water, serum, urine, saline etc. In addition, matters that require attention in general blood taking for clinical examination are that hemolysis should be avoided to a maximum degree and blood should be separated into serum and plasma as rapidly as possible. The reasons for this include the effect of hemolysis on optical measurement, the incoming and outgoing of substances such as Na, K, Cl through blood membrane, the effect of movement by blood corpuscles metabolism (i.e., transfer of lactic acid and pyruvic acid to serum by glycolysis) and the effect of the difference in concentration of the object component in blood corpuscles and in serum.

For the above reasons, blood obtained from a subject should be a sample separated into serum or plasma by centrifugation. Therefore, such pretreatment by centrifugation may not be carried out in small or private laboratories or urgent laboratories other than central laboratories in large or middle hospitals where a large amount of blood can be dealt with, and therefore the above method is not necessarily universal.

Under the circumstances of such general whole blood handling, in the field of clinical examination there is no accurate and quantitative measurement method in which whole blood can be directly used as a measurement sample without separating it into serum and plasma. Further, the measurement of blood using optical means without hemolysis is inappropriate because of high turbidity caused by erythrocyte.

OBJECTS AND SUMMARY OF THE INVENTION

In view of the foregoing, the present invention was made, and a first object is to provide an immunoassay method which can be effected easily in a short time even without pretreating blood by, e.g., a centrifuge, and a second object is to provide an immunoassay method using whole blood directly as a sample in which blood corpuscles are subjected intentionally to forcible hemolysis in a manner not to affect immunoreaction so that accurate data can be obtained in combination with various quantitative measurement reagents.

As a result of their research, the present inventors unexpectedly found that antigens or antibodies in whole blood can be determined by subjecting whole blood intentionally to forcible hemolysis in a manner not to affect agglutination reaction, as opposed to the fixed concept of general blood taking for clinical examination, that is, hemolysis should be avoided to a maximum degree and blood should be separated into serum and plasma as rapidly as possible.

To achieve the first object, the present invention comprises an immunoassay method in which antibodies or antigens in a sample are subjected to agglutination reaction with insoluble carriers onto which antigens or antibodies specifically reacting with the antibodies or antigens in the sample have been immobilized and the resulting agglutination mixture is determined for the change in its absorbance or in its scattered light by irradiation with light, wherein said sample is whole blood and the whole blood is forcibly lyzed.

In this case, the means of forcible hemolysis can include:

(1) mixing whole blood with a low osmotic solution;

(2) mixing blood with a solution of saponins for hemolysis;

(3) freezing and thawing whole blood; and (4) ultrasonicating whole blood.

Alternatively, saponins for hemolysis may be incorporated into an insoluble particle suspension reagent onto which antibody or antigen specifically reacting with antigen or antibody has been immobilized.

To achieve the second object, the immunoassay method according comprises the step of subjecting antibodies or antigens in whole blood as a sample to agglutination reaction with an insoluble particle suspension reagent onto which antigens or antibodies specifically reacting with the antibodies or antigens in the whole blood have been immobilized, the step of determining the resulting agglutination mixture for the change in its absorbance or in its scattered light by irradiation with light, and the step of calculating the hematocrit % of as follows by the sample:

$$A' = A \times 100/(100 - \text{hematocrit \%})$$

where A is the absorbance or its change or the strength of light scattering or its change actually determined, and A' is the corrected absorbance or its change or the strength of light scattering or its change assuming that the plasma component in the sample is 100%.

According to the first object, the following effects are achieved:

(1) By using a whole blood sample directly in the measurement procedure without subjecting it to pretreatment such as centrifugation etc., measurement time can be shortened, measurement costs can be reduced, and a measurement operation can be simplified. Because centrifugation is not required, the costs for a centrifuge or centrifuge tube, the operation for transferring a sample to a centrifuge tube, the time for centrifugation can be eliminated, and the opportunity for an operator to come into contact with blood can be decreased whereby the danger of infection can be significantly reduced.

(2) By subjecting blood corpuscles in whole blood to forcible hemolysis in a manner not to cause any effect on antigen-antibody reaction, the method can be combined with a measurement kit using general latex immunoturbidimetry whereby accurate measurement data can be obtain while a wide variety of applications is made feasible.

(3) By incorporating a hemolysis reagent into a latex reagent, the constitution of the measurement apparatus can be simplified and the measurement time can be reduced.

According to the present invention, accurate data can be obtained by hematocrit correction.

DETAILED DESCRIPTION OF THE PREFERRED EMBODIMENTS

Hereinafter, the present invention is described in detail by reference to Examples.

Figure 6:
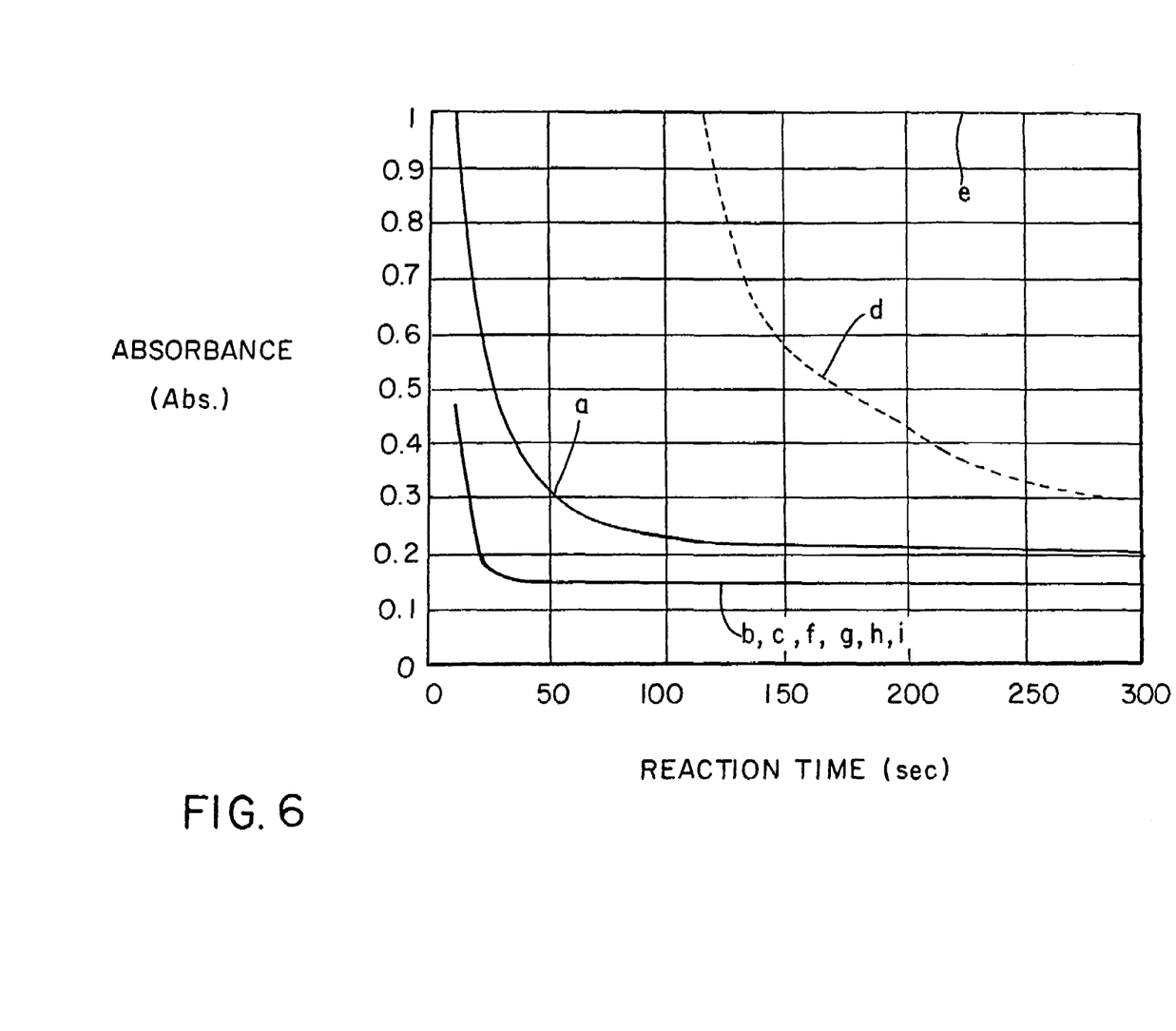
FIG. 6 is a drawing showing hemolysism reaction time course at 800 nm of whole blood having been subjected to hemolysis with aqueous solutions of various hemolysis reagents.
Figure 7:
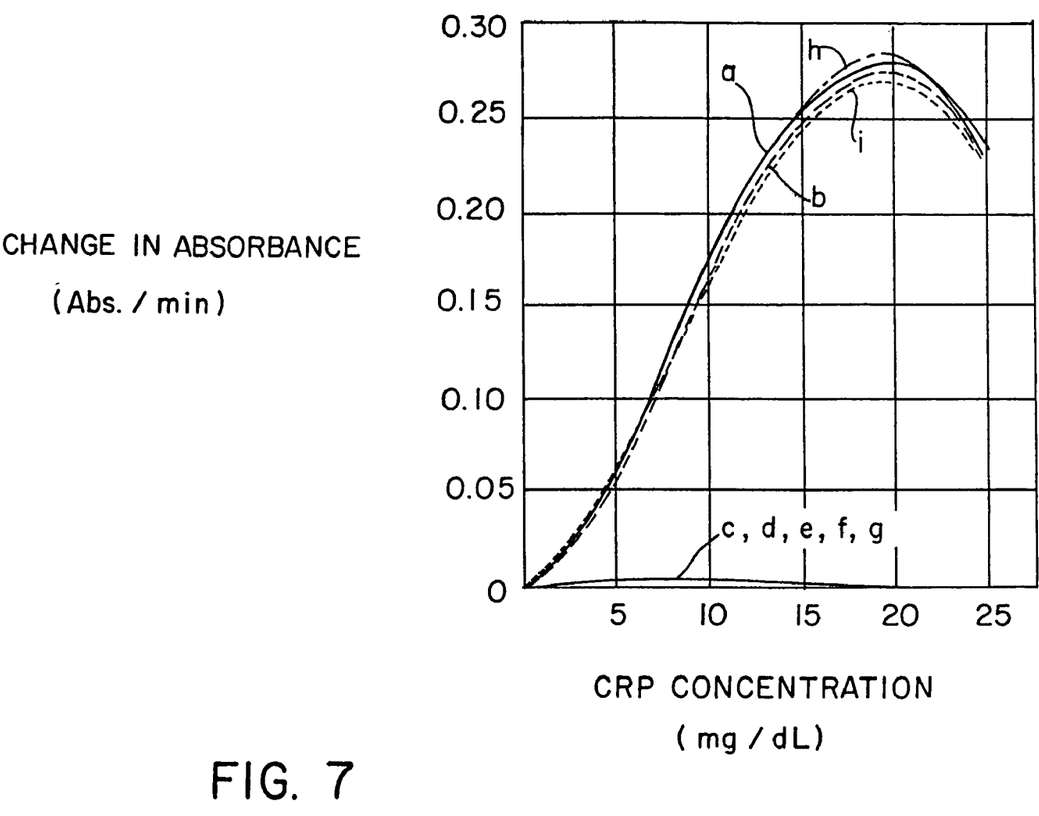
FIG. 7 is a calibration curve of change in absorbance per minute as a function of CRP concentration obtained when CRP measurement is carried out.

The reagents examined in the Example are shown in Table 1 below. The symbols "a" to "g" in Table, 1 are identical with those in FIGS. 5 to 7.

TABLE 1

|  |  | Hemolysis Method | Content (W/V %)* | Absorbance (800 nm) | ΔAbsorbance/min |
|---|---|---|---|---|---|
| Hemolysis Reagent Aqueous Solution | a | Pure Water (Deionized Water) |  | 0.204 | 0.003 |
|  | b | Saponin Aqueous Solution | 0.5 | 0.147 | 0.000 |
|  | c | TRITON X-100 ™ (Non-Ionic Surface Active Agent) | 0.5 | 0.146 | 0.000 |
|  | d | Tween-20 (Non-Ionic Surface Active Agent) | 0.5 | 0.298 | 0.055 |
|  | e | BRIJ-35 ™ (Non-Ionic Surface Active Agent) | 0.5 | 2.312 |  |
|  | f | Sodium Lauryl Sulfate (Anionic Surface Active Agent) | 0.5 | 0.176 | 0.0000 |
|  | g | Benzalkonium Chloride (Cationic Surface Active Agent) | 0.5 | 0.139 | 0.000 |
|  | h | Freezing Hemolysis |  | 0.163 | 0.000 |
|  | i | Ultrasonication Nozzle Hemolysis |  | 0.196 | 0.001 |
|  | j | Physiological Saline |  | 3.000 |  |

*W/V % = weight/volume %

EXAMPLE 1

Figure 1:
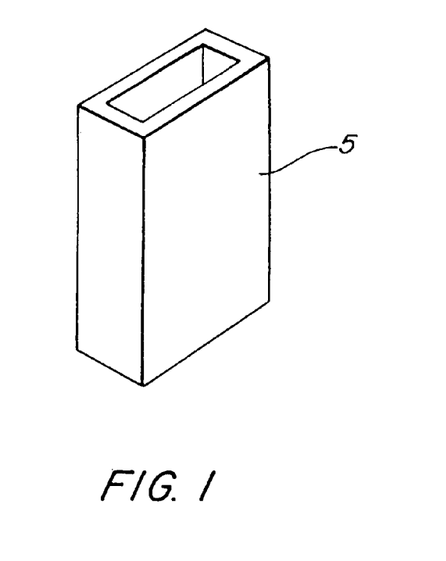
FIG. 1 is a drawing showing an example of the cell used in the method of the present invention.

Hemolysis by Hemolysis Reagents 0.04 ml of human whole blood collected in a usual manner using an EDTA-2K anticoagulant was placed in quartz cell 5 with a cell length of 5 mm as shown in FIG. 1. 2.0 ml of each of Hemolysis regent aqueous solutions to "a" to "g" shown in Table 1 was added to it and monitored for its absorption spectrum at 300 to 1000 nm (see FIG. 5) in spectrophotometer 1 (e.g., U-3410, produced by Hitachi, Ltd., Japan), for its Hemolysis reaction time course at 800 nm (see FIG. 6), for its absorbance 5 minutes after the reaction was initiated and for the change in its absorbance at 800 nm for 1 minute between 4 and 5 minutes after the reaction was initiated (see Table 1) to examine the ability of each hemolysis reagent to lyse blood.

Figure 2:
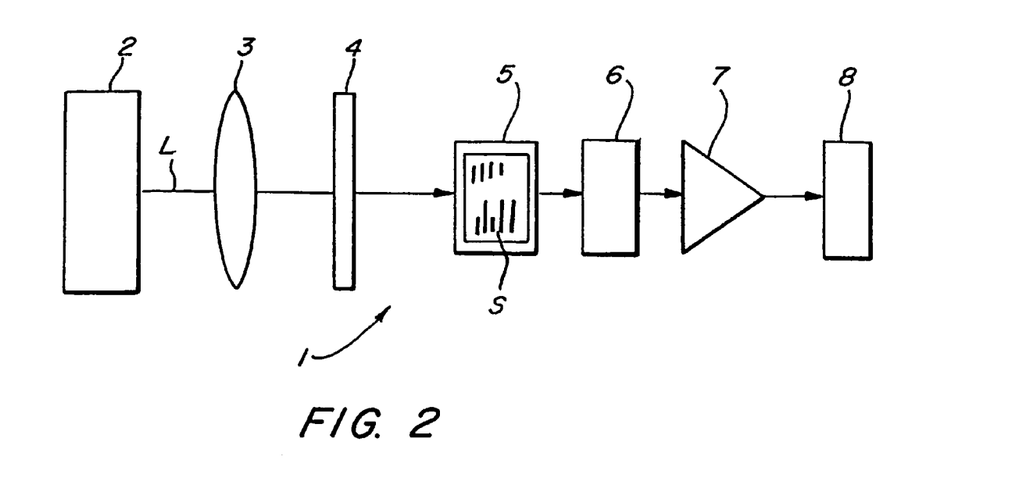
FIG. 2 is a schematic drawing showing the constitution of the spectrophotometer used in the method of the present invention.

In FIG. 2, 2 is a halogen lamp as a light source emitting irradiation light L, e.g., near infrared or infrared rays; 3 is a condensing lens; 4 is a diffraction grating; 6 is an amplifier; and 7 is an arithmetic and recording device such as a computer and 8 is a display. "S" is whole blood having been subjected to hemolysis treatment as a sample accommodated in cell 5.

Figure 5:
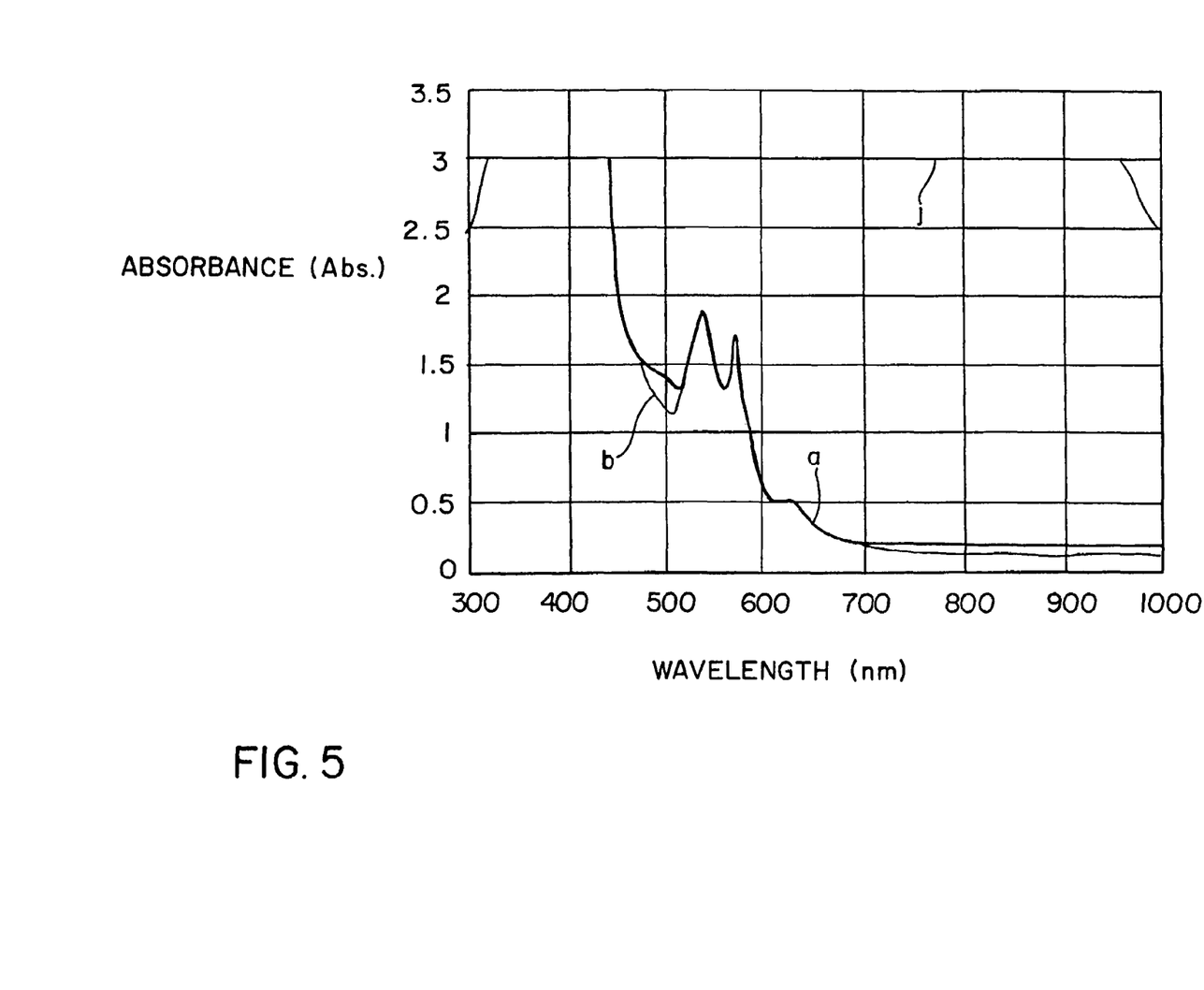
FIG. 5 is an absorption spectrum at 300 to 1000 nm of whole blood having been subjected to hemolysis with aqueous solutions of various hemolysis reagents

As shown in FIG. 5, non-lysed blood treated with the reagent "j" (psychological saline) showed an absorbance of 2.5 or more due to its turbidity at the shown wavelengths, resulting in affecting the optical detection of latex agglutination reaction. On the other hand, it was found that as shown in FIG. 5, such turbidity as described above disappeared by use of the reagent "a" (pure water) and the reagent "b" (saponin aqueous solution) so that the degree of agglutination of latex can be determined. As can be seen from Table 1 and FIG. 6, the reagent "a" (pure water), the reagent "b" (saponin), the reagent "o" (TRITON X 100™), the reagent "f" (sodium lauryl sulfate), and reagent "g" (benzalkonium chloride) have the ability to lyse whole blood in a short time.

EXAMPLE 2

Hemolysis by Freezing

Figure 3:
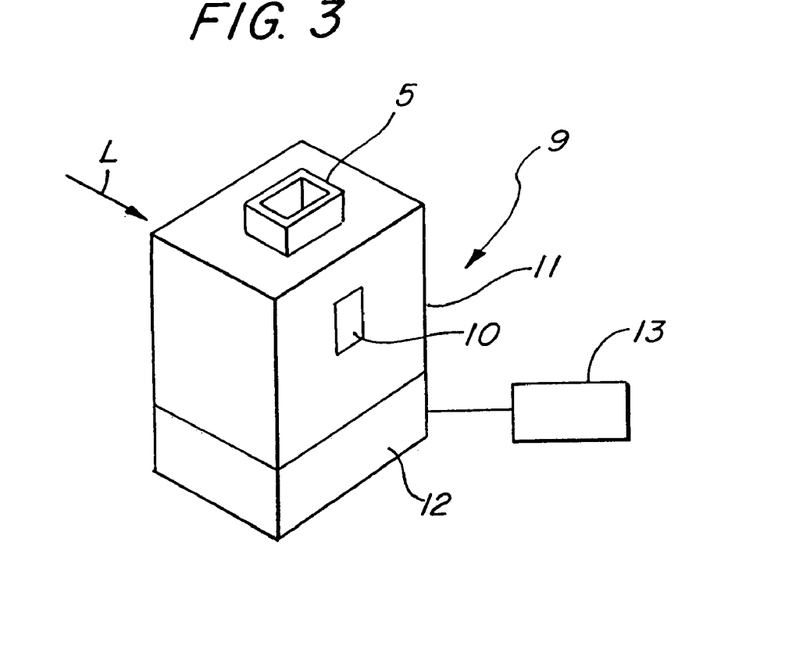
FIG. 3 is a drawing showing an example of the freezing cell holder used in the method of the present invention.

FIG. 3 shows one embodiment of freezing cell holder 9 for use in lysing whole blood, which can receive and maintain cell 5 in it and includes a Peltier element 12 (a product of e.g., Merukoa Col, Ltd.) attached to cell block 11 made of aluminum provided with photometric window 10. 13 is a power source for applying a direct current as necessary to Peltier element 12, and L is a near infrared or infrared ray from the power source 2.

0.04 ml of human whole blood collected in a usual manner using an EDTA-2K anticoagulant was accommodated in cell 5 placed in freezing cell holder 9 as shown in FIG. 3, and the human whole blood was completely frozen by applying an electric current to the Peltier element 12 for 10 minutes in a predetermined direction. Thereafter, the frozen human whole blood was thawed by applying an electric current in the reverse direction to the Peltier element 12, then diluted with 2.0 ml physiological saline, and examined for its absorbance 5 minutes after the reaction was initiated and for the change in its absorbance at 800 nm for 1 minute between 4 and 5 minutes after the reaction was initiated (see Table 1) to determine the ability of the hemolysis reagent to lyse blood. As can be seen in "h" in Table 1, human whole blood can be lysed by freezing and thawing.

EXAMPLE 3

Hemolysis by Ultrasonication

Figure 4:
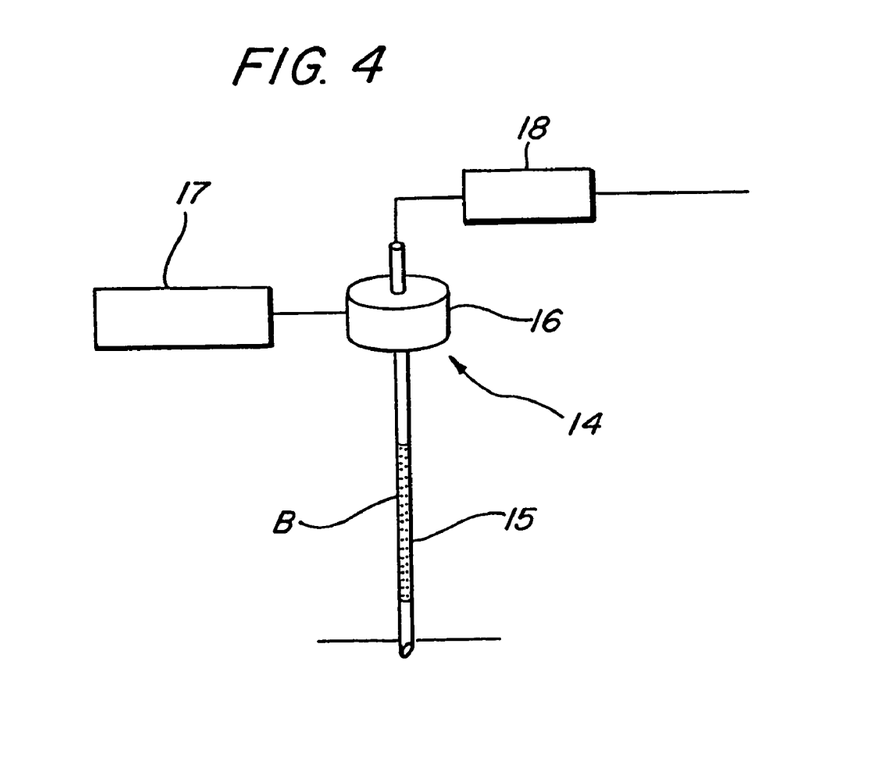
FIG. 4 is a drawing showing an example of the ultrasonication nozzle used in the method of the present invention.

FIG. 4 shows one embodiment of ultrasonic nozzle 14 for use in lyzing whole blood, which includes ultrasonic radiator 16 attached to stainless steel nozzle 15, and 17 is a radiator circuit, and 18 is a suction syringe.

0.04 ml of human whole blood obtained in a usual manner using an EDTA-2K anticoagulant was suctioned into nozzle 15, and the ultrasonic radiator 16 was run for 5 minutes to lyze human whole blood B in nozzle 15. Thereafter, the lyzed human whole blood B was accommodated in nozzle 15, then diluted with 2.0 ml physiological saline, and examined in spectrophotometer 1 for its absorption at 800 nm 5 minutes after the reaction was initiated and for the change in its absorbance for 1 minute between 4 to 5 minutes after the reaction was initiated (see Table 1) to determine the ability of the hemolysis reagent to lyse blood. As can be seen from symbol "i" in Table 1, human whole blood can be lyzed by ultrasonicating it.

C-Reactive Protein (CRP) Measurement Method 1

Preparation of Anti-CRP Antibody Sensitized Latex Solution

An about 10 mg/ml anti-human CRP rabbit antibody solution (pH 7.5, 100 mmol/l Tris-HCl buffer, 0.1% sodium amide) was added to 10 ml polystyrene latex with an average particle diameter of 0.2 μm (produced by, e.g., Japan Synthetic Rubber Co., Ltd., Japan) 10% solid content), and the mixture was allowed to stand at 30° C. one whole day and night and then centrifuged at 3600 rpm to give precipitates. 0.2 W/V % bovine serum albumin, pH 8.5, 100 mmol/l Tris-HCl buffer was added to the precipitates to prepare an anti-CRP antibody sensitized latex solution.

2) CRP Measurement Method 0.04 ml of human whole blood collected in a usual manner using an EDTA-2K anticoagulant was placed in cell 1, and 0.5 ml of each of hemolysis regent aqueous solutions "a" to "g" shown in Table 1 was added to it, and the mixture was incubated at 37° C. for 3 minutes, and 1.5 ml of the anti-human CRP antibody sensitized latex suspension prepared in item 1) above was added to it, and the change in its absorbance at 800 nm for 1 minute between 4 and 5 minutes after the reaction was initiated was determined.

Separately, a calibration curve of the above sample was prepared using a commercial latex immunoturbidimetry CRP measurement kit intended for use in examining plasma as its sample. FIG. 5 shows a calibration curve prepared using the results obtained in the above CRP measurement, and a calibration curve excellent in sensitivity as shown in symbols "a" and "b" in the figure was obtained using whole blood lysed forcibly with pure water, saponin aqueous solution "b" etc. However, the results indicated that surface active agents "c" to "g" inhibit agglutination reaction and are thus not suitable for immunoreaction, as shown in the symbols "c" to "g" in the figure.

EXAMPLE 5

CRP Measurement Method Using Blood Sample Lyzed by Freezing or Ultrasonication

The operation of dilution with physiological saline after hemolysis in Example 2 or 3 was replaced by addition of 2.0 ml of the anti-human CRP antibody sensitized latex suspension prepared in Example 4, and a change in absorbance at 800 nm for 1 minute between 4 to 5 minutes after the reaction was initiated was determined in spectrophotometer 1.

Separately, a calibration curve of the above sample was prepared using a commercial latex immunoturbidimetry CRP measurement kit intended for use in examining serum or plasma as its sample. As shown in symbols "h" and "i" in FIG. 7, a calibration curve excellent in sensitivity was obtained.

EXAMPLE 6

CRP Measurement Method 2

Figure 8:
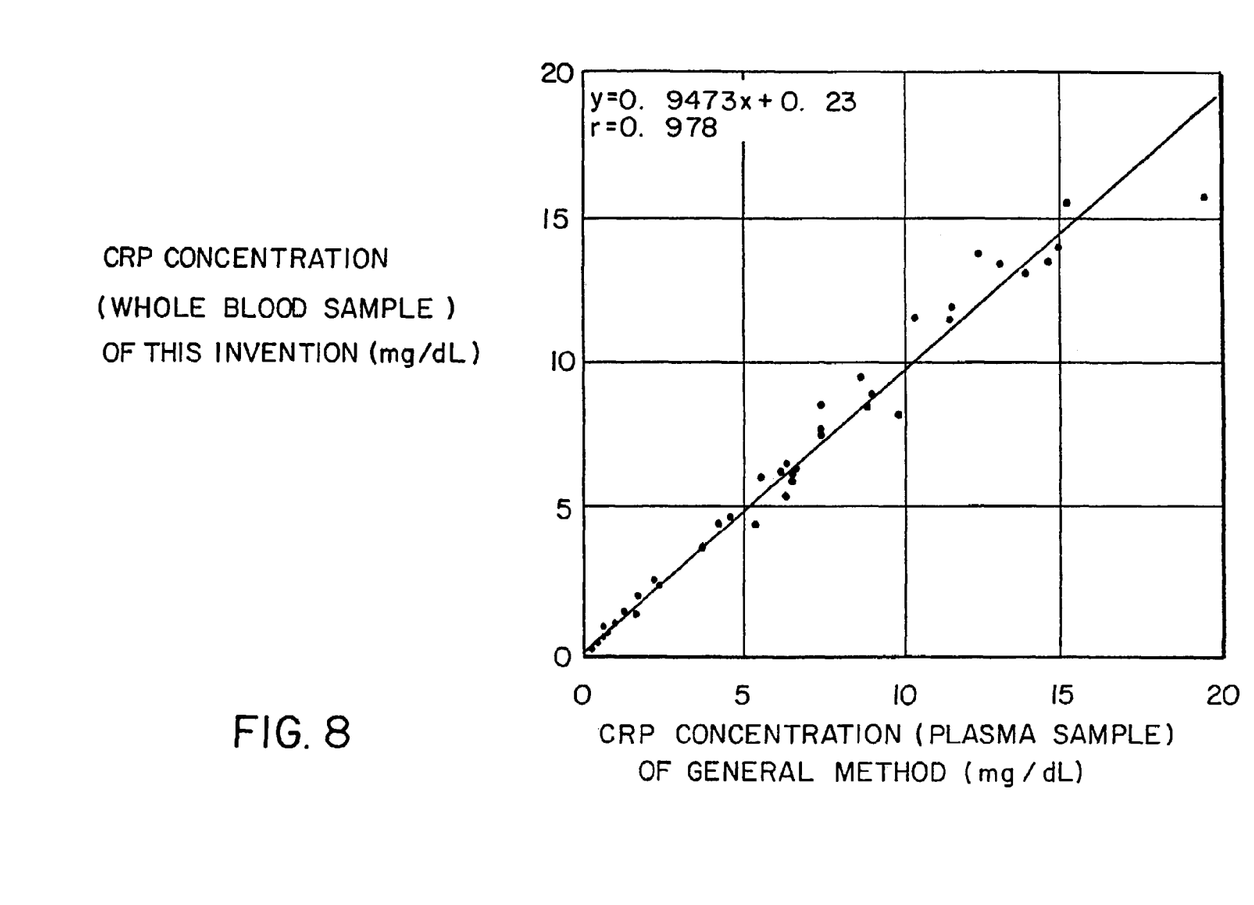
FIG. 8 is a graph showing a correlation between a whole blood sample and a plasma sample when no hematocrit correction is carried out.

The same measurement method as in Example 4 was used except that a commercial latex immunoturbidimetry CRP measurement kit was used in place of the anti-human CRP antibody sensitized latex suspension used in Example 4 and 0.5 w/v S saponin aqueous solution was used as a hemolysis reagent in order to determine a change in absorbance at 800 nm for 1 minute between 4 to 5 minutes after the reaction was initiated. A comparison between a calibration curve (n=40) using measurement values of whole blood as a sample determined according to the present invention and a calibration curve using measurement values of serum as a sample determined according to a general method indicated good correlation as shown in FIG. 8.

EXAMPLE 7

Hematocrit Correction

Figure 9:
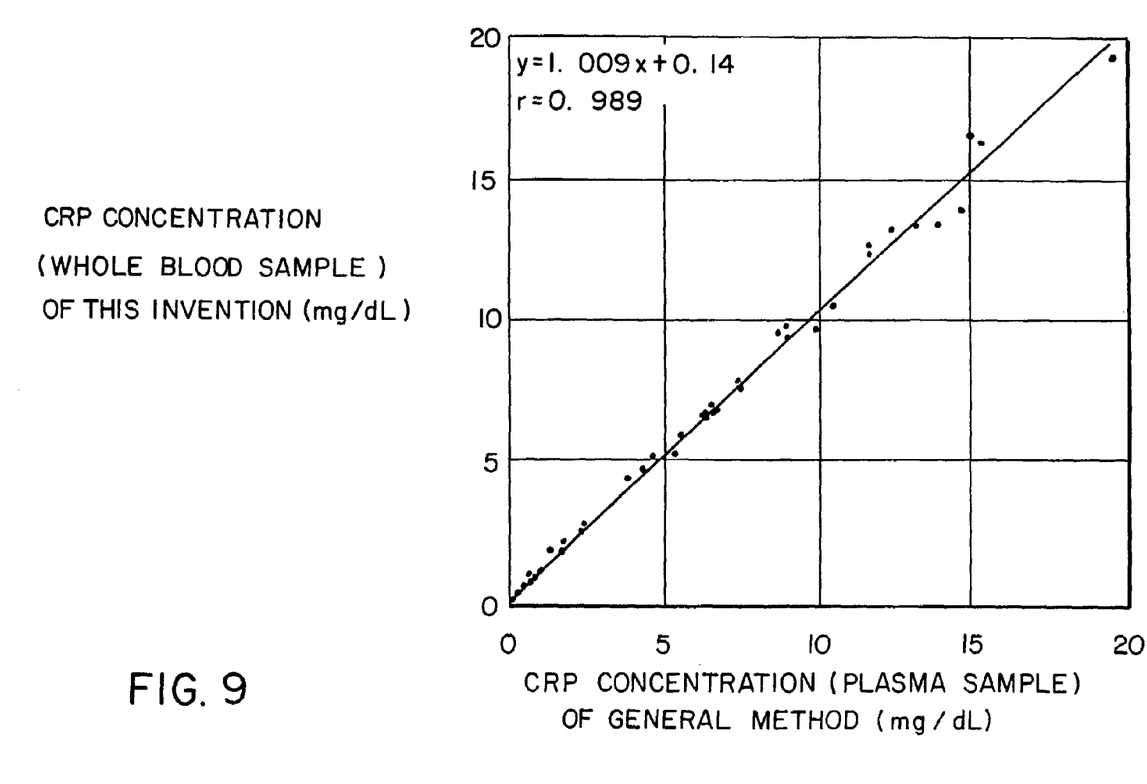
FIG. 9 is a graph showing a correlation between a whole blood sample and a plasma sample when hematocrit correction is carried out.

To correct the measurement values obtained according to the present invention in Example 6, the whole blood was simultaneously determined for its hematocrit value by means of an erythrocyte counter (e.g., LC-240A manufactured by Horiba Seisakusho K.K., Japan) using the following formula (1):

$$A' = A \times 100/(100 - \text{hematocrit \%}) \quad (1)$$

where A is the actually determined change in absorbance, and A' is its corrected change assuming that the plasma component in the sample is 100%. A comparison (n=40) between the measurement values thus corrected and the measurement values determined in a general method using serum as a sample indicated further improved correlation as compared with that of Example 6, as shown in FIG. 9.

In the Examples above, the change in absorbance of an agglutination mixture by light irradiation was determined; alternatively, the change in scattered light may be determined.

The present invention is practiced in the embodiments described above and demonstrates the following effects:

According to the present first invention, measurement time can be shortened, measurement costs can be reduced, and measurement operation can be simplified because a whole blood sample can be used directly without subjecting it to pretreatment such as centrifugation, etc. Further, the opportunity for an operator to come into contact with blood can be decreased and the danger of infection can be significantly reduced.

According to the present second invention, accurate data can be obtained by conducting hematocrit correction.

What is claimed is:

1. A particle agglutination immunoassay method of quantifying an antigen in a sample of whole blood, comprising the steps of:
   providing a sample of the whole blood;
   adding a hemolysis reagent to the sample of whole blood for hemolysing blood corpuscles in the sample of whole blood and enabling a subsequent immunoreaction;
   adding a latex reagent, including insoluble latex carriers onto which antibodies specifically reacting with the antigen in the sample of whole blood have been immobilized, to the hemolysed whole blood and to provide an agglutination reaction with the hemolysed whole blood sample thereby forming an agglutination reaction product wherein the antigen in the hemolysed whole blood sample reacts with the antibodies immobilized on the insoluble carriers to provide the agglutination reaction product;
   irradiating the agglutination reaction product in the hemolysed whole blood sample with radiation wavelength of approximately 700 nm to 1000 nm which is substantially free from absorption by both hemoglobin and the hemolysis reagent; and
   measuring, only with the wavelength of approximately 700 nm to 1000 nm, a change in absorbance of the incident radiation by the agglutination reaction product to determine the quantity of antigens in the sample.

2. The particle agglutination immunoassay method of claim 1 wherein the hemolysing reagent is saponin.

3. The particle agglutination immunoassay method of claim 1 wherein the antigen is the C-reactive protein (CRP) present in plasma in the hemolysed whole blood sample.

* * * * *